United States Patent [19]
Behan et al.

[11] Patent Number: 5,910,428
[45] Date of Patent: Jun. 8, 1999

[54] BRAIN-DERIVED MEMBRANE-ASSOCIATED CRF BINDING PROTEINS

[75] Inventors: Dominic P. Behan, San Diego; Wylie W. Vale, Jr., La Jolla; Wolfgang H. Fischer, Encinitas, all of Calif.; Philip J. Lowry, Reading Berks, United Kingdom

[73] Assignee: The Salk Institute for Biological Studies, San Diego, Calif.

[21] Appl. No.: 08/637,761

[22] PCT Filed: Nov. 7, 1994

[86] PCT No.: PCT/US94/12672

§ 371 Date: Jul. 2, 1996

§ 102(e) Date: Jul. 2, 1996

[87] PCT Pub. No.: WO95/13372

PCT Pub. Date: May 18, 1995

Related U.S. Application Data

[63] Continuation-in-part of application No. 08/149,091, Nov. 8, 1993, Pat. No. 5,587,462.

[51] Int. Cl.⁶ .............................. C07H 21/04; C12P 21/02
[52] U.S. Cl. ......................................... 435/69.1; 536/23.5
[58] Field of Search ........................... 435/69.1; 536/23.5

[56] References Cited

FOREIGN PATENT DOCUMENTS

WO 9213074  8/1992  WIPO .
WO 94/10333  5/1994  WIPO .

OTHER PUBLICATIONS

*Society for Neuroscience Abstracts*, vol. 19, 1–3, Nov. 7, 1993, p. A414, "Purification, of three CFR–binding protein subtypes from sheep brain", Behan, et al., (23rd Annual Meeting of the Society for Neuroscience, Washington, D.C. Nov. 7–12, 1993).

*Nature*, vol. 349, Jan. 31, 1991, London GB, pp. 423–426, "Cloning and characterization of the cDNAs for human and rat corticotropin releasing factor–binding proteins", Behan et al.

*Primary Examiner*—Paula K. Hutzell
*Assistant Examiner*—Stephen Gucker
*Attorney, Agent, or Firm*—Fitch, Even, Tabin & Flannery

[57] ABSTRACT

Isolated, substantially pure mammalian brain-derived membrane-associated CRF-binding proteins and biologically active fragments thereof are provided as well as isolated and purified DNA fragments which encode the CRF binding proteins or biologically active fragments thereof or homologs of other mammalian species. By administering an amount of such CRF binding protein or a fragment thereof effective to modulate receptor activation, it is possible to modulate the action of CRF upon (a) the brain and nervous system, (b) the pituitary particularly for production of ACTH, beta endorphin and cortisol, (c) sites of inflammation, (d) the placenta, (e) the adrenal glands, (f) the gonads or (g) the gastrointestinal tract. Administration of an N-terminal fragment of the protein increases the binding site density for CRF and thus modulates its biological effect in vivo.

12 Claims, No Drawings

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
      (A) LENGTH: 295 amino acids
      (B) TYPE: amino acid
      (C) STRANDEDNESS: single
      (D) TOPOLOGY: unknown (ii) MOLECULE TYPE: protein (xi) SEQUENCE DESCRIPTION: SEQ ID NO: 1:

```
Glu Ala Val Asp His Asp Pro Phe Pro His Leu Ala Gly Gly Ala Ser
1               5                   10                  15

Pro Lys Arg Glu Leu Glu Gly Glu Pro Leu Tyr Arg Arg Ala Leu Arg
                20                  25                  30

Cys Val Asp Met Leu Ser Leu Gln Gly Gln Phe Thr Phe Thr Ala Asp
            35                  40                  45

Arg Arg Gln Leu His Cys Ala Thr Phe Phe Ile Ala Glu Pro Glu Glu
        50                  55                  60

Phe Ile Thr Ile His Tyr Asp Leu Val Ser Ile Asp Cys Leu Arg Gly
65                  70                  75                  80

Asp Ile Leu Gln Val Phe Asp Gly Trp Ile Leu Lys Gly Glu Lys Phe
```

```
                        85                  90                  95
Pro Ser Ser Gln Asp His Pro Leu Pro Thr Thr Glu Arg Tyr Val Asp
                100                 105                 110
Phe Cys Asp Ser Gly Leu Ser Arg Arg Ser Ile Arg Ser Ser Gln Asn
                115                 120                 125
Val Ala Met Ile Phe Phe Arg Val His Glu Pro Gly Asn Gly Phe Thr
            130                 135                 140
Ile Thr Val Lys Thr Glu Pro Asn Leu Phe Pro Cys Asn Ile Ile Ser
145                 150                 155                 160
Gln Thr Pro Asn Gly Arg Phe Thr Leu Val Met Pro His Gln His Arg
                165                 170                 175
Asn Cys Ser Phe Ser Ile Ile Tyr Pro Val Ala Ile Lys Ile Ser Asp
            180                 185                 190
Leu Thr Leu Gly His Leu Asn Gly Leu Gln Leu Lys Lys Ser Ser Ala
            195                 200                 205
Gly Cys Gly Gly Ile Gly Asp Phe Val Glu Leu Leu Gly Gly Thr Gly
        210                 215                 220
Leu Asp Pro Ser Lys Met Leu Leu Ala Asp Leu Cys Tyr Pro Leu
225                 230                 235                 240
Arg Gly Pro Ala Gln Met Lys Val Gly Cys Asp His Thr Val Leu Arg
                245                 250                 255
Met Val Ser Ser Gly Lys His Ile Asn Arg Val Thr Phe Glu Tyr Arg
                260                 265                 270
Gln Leu Glu Pro Tyr Glu Leu Glu Asn Pro Asn Gly Asn Ser Ile Gln
                275                 280                 285
Glu Phe Cys Leu Ser Thr Leu
                290                 295
```

(2) INFORMATION FOR SEQ ID NO: 2:

(i) SEQUENCE CHARACTERISTICS:
        (A) LENGTH: 258 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 2:

```
Glu Ala Val Asp His Asp Pro Phe Pro His Leu Ala Gly Gly Ala Ser
1               5                   10                  15
Pro Lys Arg Glu Leu Glu Gly Glu Pro Glu Glu Phe Ile Thr Ile His
                20                  25                  30
Tyr Asp Leu Val Ser Ile Asp Cys Leu Arg Gly Asp Ile Leu Gln Val
            35                  40                  45
Phe Asp Gly Trp Ile Leu Lys Gly Glu Lys Phe Pro Ser Ser Gln Asp
        50                  55                  60
His Pro Leu Pro Thr Thr Glu Arg Tyr Val Asp Phe Cys Asp Ser Gly
65                  70                  75                  80
Leu Ser Arg Arg Ser Ile Arg Ser Ser Gln Asn Val Ala Met Ile Phe
                85                  90                  95
Phe Arg Val His Glu Pro Gly Asn Gly Phe Thr Ile Thr Val Lys Thr
                100                 105                 110
Glu Pro Asn Leu Phe Pro Cys Asn Ile Ile Ser Gln Thr Pro Asn Gly
            115                 120                 125
Arg Phe Thr Leu Val Met Pro His Gln His Arg Asn Cys Ser Phe Ser
        130                 135                 140
```

```
Ile Ile Tyr Pro Val Ala Ile Lys Ile Ser Asp Leu Thr Leu Gly His
145                 150                 155                 160

Leu Asn Gly Leu Gln Leu Lys Lys Ser Ser Ala Gly Cys Gly Gly Ile
            165                 170                 175

Gly Asp Phe Val Glu Leu Leu Gly Gly Thr Gly Leu Asp Pro Ser Lys
        180                 185                 190

Met Leu Leu Leu Ala Asp Leu Cys Tyr Pro Leu Arg Gly Pro Ala Gln
    195                 200                 205

Met Lys Val Gly Cys Asp His Thr Val Leu Arg Met Val Ser Ser Gly
    210                 215                 220

Lys His Ile Asn Arg Val Thr Phe Glu Tyr Arg Gln Leu Glu Pro Tyr
225                 230                 235                 240

Glu Leu Glu Asn Pro Asn Gly Asn Ser Ile Gln Glu Phe Cys Leu Ser
                245                 250                 255

Thr Leu
```

(2) INFORMATION FOR SEQ ID NO: 3:

(i) SEQUENCE CHARACTERISTICS:
      (A) LENGTH: 552 base pairs
      (B) TYPE: nucleic acid
      (C) STRANDEDNESS: unknown
      (D) TOPOLOGY: unknown (ii) MOLECULE TYPE: DNA (genomic)

(ix) FEATURE:
      (A) NAME/KEY: CDS
      (B) LOCATION: 1..552

(xi) SEQUENCE DESCRIPTION: SEQ ID NO: 3:

```
TTT CCA CAC CTC GCC GGT GGC GCC AGT CCG AAG CGG GAG CTG GAG GGG        48
Phe Pro His Leu Ala Gly Gly Ala Ser Pro Lys Arg Glu Leu Glu Gly
1               5                   10                  15

GAG CCG CTG TAC CGC CGC GCT CTG CGG TGC GTG GAC ATG CTG AGC CTC        96
Glu Pro Leu Tyr Arg Arg Ala Leu Arg Cys Val Asp Met Leu Ser Leu
                20                  25                  30

CAG GGC CAG TTC ACC TTC ACC GCC GAC CGG CGC CAG CTA CAC TGC GCC       144
Gln Gly Gln Phe Thr Phe Thr Ala Asp Arg Arg Gln Leu His Cys Ala
            35                  40                  45

ACA TTC TTC ATC GCA GAG CCG GAG GAG TTC ATC ACC ATC CAC TAC GAT       192
Thr Phe Phe Ile Ala Glu Pro Glu Glu Phe Ile Thr Ile His Tyr Asp
        50                  55                  60

CTG GTC TCC ATC GAC TGT CTG AGG GGC GAC ATC CTG CAG GTA TTT GAT       240
Leu Val Ser Ile Asp Cys Leu Arg Gly Asp Ile Leu Gln Val Phe Asp
65                  70                  75                  80

GGT TGG ATT CTC AAG GGG GAG AAA TTC CCC AGT TCC CAG GAT CAC CCT       288
Gly Trp Ile Leu Lys Gly Glu Lys Phe Pro Ser Ser Gln Asp His Pro
                85                  90                  95

CTC CCC ACC ACT GAG AGG TAC GTA GAT TTC TGT GAC AGT GGT CTG AGC       336
Leu Pro Thr Thr Glu Arg Tyr Val Asp Phe Cys Asp Ser Gly Leu Ser
            100                 105                 110

AGA AGG AGC ATC AGA TCC TCC CAG AAC GTG GCC ATG ATC TTC TTC CGG       384
Arg Arg Ser Ile Arg Ser Ser Gln Asn Val Ala Met Ile Phe Phe Arg
        115                 120                 125

GTC CAT GAG CCA GGA AAT GGA TTC ACA ATA ACC GTG AAG ACA GAG CCT       432
Val His Glu Pro Gly Asn Gly Phe Thr Ile Thr Val Lys Thr Glu Pro
130                 135                 140

AAC CTC TTC CCC TGC AAT ATC ATC TCC CAG ACC CCC AAT GGA AGG TTT       480
Asn Leu Phe Pro Cys Asn Ile Ile Ser Gln Thr Pro Asn Gly Arg Phe
145                 150                 155                 160
```

```
ACT CTG GTC ATG CCG CAT CAG CAT CGA AAC TGC AGC TTC TCC ATC ATT    528
Thr Leu Val Met Pro His Gln His Arg Asn Cys Ser Phe Ser Ile Ile
            165                 170                 175

TAT CCT GTA GCG ATC AAA ATA TCC                                    552
Tyr Pro Val Ala Ile Lys Ile Ser
            180
```

(2) INFORMATION FOR SEQ ID NO: 4:

(i) SEQUENCE CHARACTERISTICS:
        (A) LENGTH: 441 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 1..441

(xi) SEQUENCE DESCRIPTION: SEQ ID NO: 4:

```
TTT CCA CAC CTC GCC GGT GGC GCC AGT CCG AAG CGG GAG CTG GAG GGG     48
Phe Pro His Leu Ala Gly Gly Ala Ser Pro Lys Arg Glu Leu Glu Gly
 1               5                  10                  15

GAG CCG GAG GAG TTC ATC ACC ATC CAC TAC GAT CTG GTC TCC ATC GAC     96
Glu Pro Glu Glu Phe Ile Thr Ile His Tyr Asp Leu Val Ser Ile Asp
                20                  25                  30

TGT CTG AGG GGC GAC ATC CTG CAG GTC TTT GAT GGT TGG ATT CTC AAG    144
Cys Leu Arg Gly Asp Ile Leu Gln Val Phe Asp Gly Trp Ile Leu Lys
            35                  40                  45

GGG GAG AAA TTC CCC AGT TCC CAG GAT CAC CCT CTC CCC ACC ACT GAG    192
Gly Glu Lys Phe Pro Ser Ser Gln Asp His Pro Leu Pro Thr Thr Glu
 50                  55                  60

AGG TAC GTA GAT TTC TGT GAC AGT GGT CTG AGC AGA AGG AGC ATC AGA    240
Arg Tyr Val Asp Phe Cys Asp Ser Gly Leu Ser Arg Arg Ser Ile Arg
 65                  70                  75                  80

TCC TCC CAG AAC GTG GCC ATG ATC TTC TTC CGG GTC CAT GAG CCA GGA    288
Ser Ser Gln Asn Val Ala Met Ile Phe Phe Arg Val His Glu Pro Gly
                85                  90                  95

AAT GGA TTC ACA ATA ACC GTG AAG ACA GAG CCT AAC CTC TTC CCC TGC    336
Asn Gly Phe Thr Ile Thr Val Lys Thr Glu Pro Asn Leu Phe Pro Cys
            100                 105                 110

AAT AGC ATC TCC CAG ACC CCG AAT GGA AGG TTT ACT CTG GTC ATG CCG    384
Asn Ser Ile Ser Gln Thr Pro Asn Gly Arg Phe Thr Leu Val Met Pro
        115                 120                 125

CAT CAG CAT CGC AAC TGC AGC TTC TCC ATC ATT TAT CCT GTA GCG ATC    432
His Gln His Arg Asn Cys Ser Phe Ser Ile Ile Tyr Pro Val Ala Ile
130                 135                 140

AAA ATA TCC                                                        441
Lys Ile Ser
145
```

(2) INFORMATION FOR SEQ ID NO: 5:

(i) SEQUENCE CHARACTERISTICS:
        (A) LENGTH: 678 base pairs
        (B) TYPE: nucleic acid
        (C) STRANDEDNESS: unknown
        (D) TOPOLOGY: unknown (ii) MOLECULE TYPE: cDNA to mRNA (ix) FEATURE:
        (A) NAME/KEY: CDS
        (B) LOCATION: 1..678

(xi) SEQUENCE DESCRIPTION: SEQ ID NO: 5:

```
GAT CTG GTC TCC ATC GAC TGT CTG AGG GGC GAC ATC CTG CAG GTA TTT       48
Asp Leu Val Ser Ile Asp Cys Leu Arg Gly Asp Ile Leu Gln Val Phe
 1               5                  10                  15

GAT GGT TGG ATT CTC AAG GGG GAG AAA TTC CCC AGT TCC CAG GAT CAC       96
Asp Gly Trp Ile Leu Lys Gly Glu Lys Phe Pro Ser Ser Gln Asp His
                20                  25                  30

CCT CTC CCC ACC ACT GAG AGG TAC GTA GAT TTC TGT GAC AGT GGT CTG      144
Pro Leu Pro Thr Thr Glu Arg Tyr Val Asp Phe Cys Asp Ser Gly Leu
            35                  40                  45

AGC AGA AGG AGC ATC AGA TCC TCC CAG AAC GTG GCC ATG ATC TTC TTC      192
Ser Arg Arg Ser Ile Arg Ser Ser Gln Asn Val Ala Met Ile Phe Phe
        50                  55                  60

CGG GTC CAT GAG CCA GGA AAT GGA TTC ACA ATA ACC GTG AAG ACA GAG      240
Arg Val His Glu Pro Gly Asn Gly Phe Thr Ile Thr Val Lys Thr Glu
 65                 70                  75                  80

CCT AAC CTC TTC CCC TGC AAT ATC ATC TCC CAG ACC CCG AAT GGA AGG      288
Pro Asn Leu Phe Pro Cys Asn Ile Ile Ser Gln Thr Pro Asn Gly Arg
                85                  90                  95

TTT ACT CTG GTC ATG CCG CAT CAG CAT CGC AAC TGC AGC TTC TCC ATC      336
Phe Thr Leu Val Met Pro His Gln His Arg Asn Cys Ser Phe Ser Ile
            100                 105                 110

ATT TAT CCT GTA GCG ATC AAA ATA TCC GAT CTC ACC CTG GGA CAC TTA      384
Ile Tyr Pro Val Ala Ile Lys Ile Ser Asp Leu Thr Leu Gly His Leu
        115                 120                 125

AAT GGT CTG CAG TTA AAG AAG TCC TCC GCA GGC TGT GGG GGA ATA GGA      432
Asn Gly Leu Gln Leu Lys Lys Ser Ser Ala Gly Cys Gly Gly Ile Gly
130                 135                 140

GAC TTT GTG GAG CTG CTG GGA GGA ACT GGT TTG GAC CCT TCC AAG ATG      480
Asp Phe Val Glu Leu Leu Gly Gly Thr Gly Leu Asp Pro Ser Lys Met
145                 150                 155                 160

CTG CTT TTA GCT GAT CTC TGC TAC CCT TTA CGT GGC CCA GCC CAG ATG      528
Leu Leu Leu Ala Asp Leu Cys Tyr Pro Leu Arg Gly Pro Ala Gln Met
                165                 170                 175

AAA GTT GGC TGT GAC CAC ACG GTA CTG CGC ATG GTC TCC AGT GGA AAA      576
Lys Val Gly Cys Asp His Thr Val Leu Arg Met Val Ser Ser Gly Lys
            180                 185                 190

CAC ATA AAT CGT GTG ACT TTT GAG TAT CGA CAG CTG GAA CCA TAT GAG      624
His Ile Asn Arg Val Thr Phe Glu Tyr Arg Gln Leu Glu Pro Tyr Glu
        195                 200                 205

CTG GAG AAC CCG AAT GGA AAC AGT ATC CAG GAA TTC TGT TTG TCT ACC      672
Leu Glu Asn Pro Asn Gly Asn Ser Ile Gln Glu Phe Cys Leu Ser Thr
    210                 215                 220

CTT TGA                                                              678
Leu
225
```

(2) INFORMATION FOR SEQ ID NO: 6:

(i) SEQUENCE CHARACTERISTICS:
        (A) LENGTH: 298 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 6:

```
Tyr Leu Glu Leu Arg Glu Ala Ala Asp Tyr Asp Pro Phe Leu Leu Phe
 1               5                  10                  15

Ser Ala Asn Leu Lys Arg Asp Val Ala Gly Glu Gln Pro Tyr Arg Arg
```

```
                20                  25                  30
        Ala Leu Arg Cys Leu Asp Met Leu Ser Leu Gln Gly Gln Phe Thr Phe
                     35                  40                  45

Thr Ala Asp Arg Pro Gln Leu His Cys Ala Ala Phe Phe Ile Ser Glu
         50                  55                  60

Pro Glu Glu Phe Ile Thr Ile His Tyr Asp Gln Val Ser Ile Asp Cys
         65                  70                  75                  80

Gln Gly Gly Asp Phe Leu Lys Val Phe Asp Gly Trp Ile Leu Lys Gly
                         85                  90                  95

Glu Lys Phe Pro Ser Ser Gln Asp His Pro Leu Pro Ser Ala Glu Arg
                        100                 105                 110

Tyr Ile Asp Phe Cys Glu Ser Gly Leu Ser Arg Arg Ser Ile Arg Ser
                        115                 120                 125

Ser Gln Asn Val Ala Met Ile Phe Phe Arg Val His Glu Pro Gly Asn
                    130                 135                 140

Gly Phe Thr Leu Thr Ile Lys Thr Asp Pro Asn Leu Phe Pro Cys Asn
        145                 150                 155                 160

Val Ile Ser Gln Thr Pro Asn Gly Lys Phe Thr Leu Val Val Pro His
                        165                 170                 175

Gln His Arg Asn Cys Ser Phe Ser Ile Ile Tyr Pro Val Val Ile Lys
                        180                 185                 190

Ile Ser Asp Leu Thr Leu Gly His Val Asn Gly Leu Gln Leu Lys Lys
                    195                 200                 205

Ser Ser Ala Gly Cys Glu Gly Ile Gly Asp Phe Val Glu Leu Leu Glu
                210                 215                 220

Gly Thr Gly Leu Asp Pro Ser Lys Met Thr Pro Leu Ala Asp Leu Cys
        225                 230                 235                 240

Tyr Pro Phe His Gly Pro Ala Gln Met Lys Val Gly Cys Asp Asn Thr
                        245                 250                 255

Val Val Arg Met Val Ser Ser Gly Lys His Val Asn Arg Val Thr Phe
                    260                 265                 270

Glu Tyr Arg Gln Leu Glu Pro Tyr Glu Leu Glu Asn Pro Asn Gly Asn
                    275                 280                 285

Ser Ile Gly Glu Phe Cys Leu Ser Gly Leu
                    290                 295
```

(2) INFORMATION FOR SEQ ID NO: 7:

(i) SEQUENCE CHARACTERISTICS:
        (A) LENGTH: 975 base pairs
        (B) TYPE: nucleic acid
        (C) STRANDEDNESS: unknown
        (D) TOPOLOGY: unknown (ii) MOLECULE TYPE: cDNA to mRNA (ix) FEATURE:
        (A) NAME/KEY: CDS
        (B) LOCATION: 1..975

(xi) SEQUENCE DESCRIPTION: SEQ ID NO: 7:

```
ATG GCC CCC ACT TTG AAA CTT CAG TGT CAC TTC ATT CTG GTC TGC CTG        48
Met Ala Pro Thr Leu Lys Leu Gln Cys His Phe Ile Leu Val Cys Leu
 1               5                  10                  15

CTG GCT CTA AGA GGA GAG AGC CGG TAC CTG GAG CTG CGA GAA GCA GTG        96
Leu Ala Leu Arg Gly Glu Ser Arg Tyr Leu Glu Leu Arg Glu Ala Val
                 20                  25                  30

GAC CAC GAC CCT TTT CCA CAC CTC GCC GGT GGC GCC AGT CCG AAG CGG       144
Asp His Asp Pro Phe Pro His Leu Ala Gly Gly Ala Ser Pro Lys Arg
```

```
                35                    40                    45
GAG CTG GAG GGG GAG CCG CTG TAC CGC CGC GCT CTG CGG TGC GTG GAC       192
Glu Leu Glu Gly Glu Pro Leu Tyr Arg Arg Ala Leu Arg Cys Val Asp
         50                    55                    60

ATG CTG AGC CTC CAG GGC CAG TTC ACC TTC ACC GCC GAC CGG CGC CAG       240
Met Leu Ser Leu Gln Gly Gln Phe Thr Phe Thr Ala Asp Arg Arg Gln
 65                    70                    75                    80

CTA CAC TGC GCC ACA TTC TTC ATC GCA GAG CCG GAG GAG TTC ATC ACC       288
Leu His Cys Ala Thr Phe Phe Ile Ala Glu Pro Glu Glu Phe Ile Thr
                      85                    90                    95

ATC CAC TAC GAT CTG GTC TCC ATC GAC TGT CTG AGG GGC GAC ATC CTG       336
Ile His Tyr Asp Leu Val Ser Ile Asp Cys Leu Arg Gly Asp Ile Leu
                 100                   105                   110

CAG GTA TTT GAT GGT TGG ATT CTC AAG GGG GAG AAA TTC CCC AGT TCC       384
Gln Val Phe Asp Gly Trp Ile Leu Lys Gly Glu Lys Phe Pro Ser Ser
             115                   120                   125

CAG GAT CAC CCT CTC CCC ACC ACT GAG AGG TAC GTA GAT TTC TGT GAC       432
Gln Asp His Pro Leu Pro Thr Thr Glu Arg Tyr Val Asp Phe Cys Asp
130                   135                   140

AGT GGT CTG AGC AGA AGG AGC ATC AGA TCC TCC CAG AAC GTG GCC ATG       480
Ser Gly Leu Ser Arg Arg Ser Ile Arg Ser Ser Gln Asn Val Ala Met
145                   150                   155                   160

ATC TTC TTC CGG GTC CAT GAG CCA GGA AAT GGA TTC ACA ATA ACC GTG       528
Ile Phe Phe Arg Val His Glu Pro Gly Asn Gly Phe Thr Ile Thr Val
                      165                   170                   175

AAG ACA GAG CCT AAC CTC TTC CCC TGC AAT ATC ATC TCC CAG ACC CCG       576
Lys Thr Glu Pro Asn Leu Phe Pro Cys Asn Ile Ile Ser Gln Thr Pro
                 180                   185                   190

AAT GGA AGG TTT ACT CTG GTC ATG CCG CAT CAG CAT CGC AAC TGC AGC       624
Asn Gly Arg Phe Thr Leu Val Met Pro His Gln His Arg Asn Cys Ser
             195                   200                   205

TTC TCC ATC ATT TAT CCT GTA GCG ATC AAA ATA TCC GAT CTC ACC CTG       672
Phe Ser Ile Ile Tyr Pro Val Ala Ile Lys Ile Ser Asp Leu Thr Leu
        210                   215                   220

GGA CAC TTA AAT GGT CTG CAG TTA AAG AAG TCC TCC GCA GGC TGT GGG       720
Gly His Leu Asn Gly Leu Gln Leu Lys Lys Ser Ser Ala Gly Cys Gly
225                   230                   235                   240

GGA ATA GGA GAC TTT GTG GAG CTG CTG GGA GGA ACT GGT TTG GAC CCT       768
Gly Ile Gly Asp Phe Val Glu Leu Leu Gly Gly Thr Gly Leu Asp Pro
                      245                   250                   255

TCC AAG ATG CTG CTT TTA GCT GAT CTC TGC TAC CCT TTA CGT GGC CCA       816
Ser Lys Met Leu Leu Leu Ala Asp Leu Cys Tyr Pro Leu Arg Gly Pro
                 260                   265                   270

GCC CAG ATG AAA GTT GGC TGT GAC CAC ACG GTG CTG CGC ATG GTC TCC       864
Ala Gln Met Lys Val Gly Cys Asp His Thr Val Leu Arg Met Val Ser
             275                   280                   285

AGT GGA AAA CAT ATA AAT CGT GTG ACT TTT GAG TAT CGT CAG CTG GAA       912
Ser Gly Lys His Ile Asn Arg Val Thr Phe Glu Tyr Arg Gln Leu Glu
        290                   295                   300

CCA TAT GAG CTG GAA AAC CCG AAT GGA AAC AGT ATC CAG GAA TTC TGT       960
Pro Tyr Glu Leu Glu Asn Pro Asn Gly Asn Ser Ile Gln Glu Phe Cys
305                   310                   315                   320

TTG TCT ACC CTT TGA                                                   975
Leu Ser Thr Leu
             325
```

BRAIN-DERIVED MEMBRANE-ASSOCIATED CRF BINDING PROTEINS

This application is a continuation-in-part of U.S. Ser. No. 08/149,094 filed Nov. 8, 1993 and a 371 of PCT/0594/12672 (U.S. Pat. No. 5,587,462), filed Nov. 7, 1994.

This invention was made with Government support under Grants DK-26741 and HD-13527 awarded by the National Institutes of Health. The Government has certain rights in the invention. The University of Reading and the Medical Research Council of Great Britain also contributed financially to this invention.

This invention relates generally to controlling the biological effect of Corticotropin releasing-factor (CRF) in mammals and more particularly to CRF binding proteins (CRF-BP) which are expressed on cell surfaces in the brain and have a high affinity for CRF.

BACKGROUND OF THE INVENTION

Stress is the demand placed upon an organism subjected to real or perceived threat or challenge. In order to maintain homeostasis, the organism mounts an array of hormonal, autonomic and behavioral responses, some of which are common to most stressful circumstances, such as activation of the pituitary adrenal axis and sympathetic nervous system and behavioral arousal. The stress response in large part is regulated through Corticotropin-Releasing Factor (CRF), a 41-residue hypothalamic peptide that stimulates the secretion and biosynthesis of pituitary ACTH, leading to increased adrenal glucocorticoid production. This process is regulated through a negative feedback loop whereby glucocorticoids suppress CRF production.

Although originally isolated and characterized on the basis of its role in this hypothalamopituitary-adrenal (HPA) axis, CRF has been found to be distributed broadly within the central nervous system as well as in extraneural tissues, such as the adrenal glands and testes, where it may also act as a paracrine regulator or a neurotransmitter. Moreover, the involvement of CRF in affective disorders, such as depression and anorexia nervosa, and in modulating reproduction and immune responses suggests that changes in CRF expression may have important physiological consequences. For example, perturbations in the regulatory loops comprising the HPA axis often produce chronically elevated levels of circulating glucocorticoids; such patients display the physical hallmarks of Cushing's syndrome, including truncal obesity, muscle-wasting, and reduced fertility. Most cases of Cushing's syndrome are caused by ACTH-producing tumors of the pituitary or, less frequently, nonendocrine tissue. Adrenal gland tumors or ectopic adrenal tissue account for 10–30% of occurrences of the disorder, but, in contrast to the pituitary-dependent form, plasma ACTH levels are not elevated. Several patients with Cushing's syndrome have been reported with ectopic CRF-secreting tumors, leading to the proposal that CRF can chronically drive pituitary ACTH production and, in turn, glucocorticoid release. It has been suggested that excess production of CRF may cause pituitary hyperplasia, leading to microadenoma formation and excess ACTH production. That pituitary hyperplasia accompanies some CRF-secreting tumors is consistent with this proposal.

CRF is thus a very potent stimulator of the synthesis and secretion of various peptides in the human body. The rat and human species have the same CRF molecule (r/h CRF or hCRF), which is a 41-residue peptide having the structure which is set forth in U.S. Pat. No. 4,489,163. Ovine CRF (OCRF) was first characterized, and its 41-residue structure is set forth in U.S. Pat. No. 4,415,558.

Although CRF levels in human peripheral circulation are normally low, there are often elevated levels of CRF in the maternal circulation, which levels progressively increase throughout pregnancy. It has been found that the increasing concentrations of CRF in pathological cases of pregnancy, such as pregnancy-induced hypertension and pre-term labor, are substantially and significantly elevated above those found in normal pregnancies (Campbell et al., *J. Clin. Endocr. & Metab.*, 64:1054–1059, 1987).

It is believed that this maternal plasma CRF most likely originates from the placenta wherein it plays a paracrine role. Placenta cells have been shown to respond to CRF and to produce CRF and its mRNA. Even though CRF concentrations measured in late gestational maternal plasma are similar to levels reported in rat hypothalamic portal blood, which levels are capable of stimulating ACTH release in vitro, it does not appear that there is normally overproduction of ACTH during pregnancy. However, maternal plasma ACTH concentrations do increase slightly with advancing gestation.

A number of workers have used molecular cross-linking with radioiodinated CRF to identify putative ovine CRF binding proteins and receptors in brain, pituitary and AtT-20 cells which range from 40–70 kD in molecular weight. After subtraction of the molecular weight of the cross-linked CRF (~5 kD), the main protein form that was found in the pituitary gland was reported to be 70 kD, Nishimura et al., *J. Biol. Chem.*, 262, 12893 (1987). A lower molecular weight protein of about 50 kD was reported to be the major brain form; Grigoriadis, et al., *Endocrinology*, 125, 3068–3077 (1989). The heterogeneity in sizes of these proteins was thought to be possibly due to differential glycosylation because, after N-glycanase treatment, only one cross-linked species of about 40–46 kD was observed in both brain and pituitary.

There were also reports of proteins in human plasma which are capable of biologically inactivating CRF, see Linton, E. A., et al. *Clin. Endo.* 28, 315–324 (1988) and Behan, D. P., et al. *J. Endo.* 122, 23–31 (1989), the latter of which discloses a partial purification process which resulted in an isolate that has now been determined to have been no more than about 50% pure. The purification of the isolated protein was ultimately accomplished, and sequencing of the pure compound provided sufficient amino acid sequence information to clone the DNA encoding this protein, which is now referred to as human serum hCRF-binding protein (hCRF-BP) [SEQ ID NO:6], E. Potter, et al., *Nature*, 349, 423–426 (Jan. 31 1991). It has been proposed that the role of this protein substance might be the prevention of inappropriate pituitary-adrenal stimulation during pregnancy, and recombinant rat and human serum CRF-BPs have now been expressed in COS cells. They have been found to bind to the 41-residue CRF with high affinity, so as to be capable of therapeutically modulating the effect of CRF.

Some additional preliminary work has been done trying to isolate CRF receptors. Grigoriadis and DeSouza, *J. Biol. Chem.*, 263, 10927–10931 (1988) and Grigoriadis, et al., supra, speculated that the molecular weight of the brain CRF receptor to be about 58 kD, less the MW of ovine CRF; however, their characterizations have been limited to estimates of the molecular weight of this protein by SDS-PAGE analysis of covalent complexes formed by chemical crosslinking between the receptor and $^{125}$I-CRF which are present within crude extracts containing a myriad of other proteins. They have not published more definitive information with regard to the CRF receptors and thus have not enabled others to determine or utilize the receptor structures.

Synaptic membrane CRF binding sites in the mammalian brain are integral to central relays for several sensory modalities including the olfactory bulb which comprises prominent sites of CRF-BP gene expression. The presence of membrane-associated CRF receptors in the mammalian brain are demonstrated inter alia by the presence of binding proteins in important cell groups which mask the immunodetection of CRF peptides present for the regulation of corticotropin production and intercellular communication of the central nervous system. Present studies in this field are aimed at determining how the expression of membrane-associated brain CRF-BPs are regulated by stress and corticosteroid influences.

In order to study the structure and biological characteristics of brain-derived membrane-associated proteins which bind to CRF and also to study the role played by these binding proteins in the responses of various cell populations to CRF stimulation, or in order to use them effectively in therapy, as components in affinity columns, diagnosis or assay, homogeneous compositions of the binding proteins are needed. Such compositions are theoretically available via purification of solubilized proteins expressed by cultured cells; however, even in cell lines known to express detectable levels of CRF receptors, such is present as a very minor component of total cellular proteins. It is therefore desirable that the nature and the structure of such membrane-associated CRF binding proteins be ascertained so that these proteins can be provided in sufficient quantity to allow them to be utilized for screening of compounds for drug design, for therapy by modulation of transactivation of CRF receptors by means of competition for tissue binding sites, for affinity columns and for other appropriate purposes.

SUMMARY OF THE INVENTION

Several membrane-associated CRF-BP proteins have now been isolated from sheep (ovine) brain and characterized; they exhibit an ability to bind to hCRF which has been immobilized on a solid-phase matrix. Proteins of molecular weights of about 33 and about 35 kD have been obtained; each binds to $^{125}$I-radiolabeled human CRF and to ovine CRF and can be cross-linked thereto using a bifunctional cross-linking agent, such as disuccinimidyl suberate, if desired. It is found that the 33 kD CRF-BP and the 35 kD CRF-BP complex with each other; the complex is through the N-terminal portion of the 35 kD protein, as identified in an assay which uses an antibody raised thereagainst. Biologically active, naturally occurring proteolytic products of the 35 kD ovine brain-derived membrane-associated CRF-BP have also been identified as the N-terminal fragments of the 35 kD protein which are active in complexing with the 33 kD CRF-BP and in causing the in vivo dissociation of the afore-described 33 kD/35 kD protein complex. An N-terminal fragment of hCRF-BP (SEQ ID NO:6) is similarly biologically active to cause dissociation of complexes of membrane-associated CRF-BPS. Biologically active CRF binding protein counterparts of the 35 and 33 kD ovine proteins have also been identified which have a deletion of an internal amino acid sequence that is believed to be the result of alterative gene splicing.

The present invention particularly provides mammalian, brain-derived, membrane-associated CRF binding proteins, including human homologs, which can be employed to complex with CRF and thereby modulate CRF actions in mammals by means of antagonistic association and which can also be employed for the design of more effective analogs and drugs. The peptides of the present invention are also useful for screening compounds in competitive binding assays in order to determine their relative affinities for CRF receptors and the like. These peptides are also useful for coupling to affinity column matrices for the purification of CRF from biological samples. The N-terminal fragments are similarly useful in purifying and assaying for CRF-BP.

DETAILED DESCRIPTION OF PREFERRED EMBODIMENTS

CRF stimulates the biosynthesis and secretion of ACTH and β-endorphin-like immunoactivities (β-END-LI) through a plasma membrane receptor protein which functions in combination with membrane-associated binding proteins described herein. The proteins disclosed herein include but are not limited to those isolated from ovine brain. Biologically active analogs can be readily constructed by those skilled in the art once the amino acid sequence is known.

Unless defined otherwise, all technical and scientific terms used herein have the same meaning as is commonly understood by one of skill in the art to which this invention belongs. The amino acids, which occur in the various amino acid sequences appearing herein, are identified according to their well-known, three-letter or one-letter abbreviations. The nucleotides, which occur in the various DNA fragments, are designated with the standard single-letter designations used routinely in the art.

The term homology is used in its usual and well known sense of indicating correspondence between members in a sequence, e.g. either on an amino acid (AA) level or at the nucleotide level. For purposes of this application, by homologous is meant having at least about 70% correspondence, by substantially homologous is meant having a correspondence of at least about 80%, and by highly homologous is meant having a correspondence of at least about 90% or preferably about 95% or higher.

Polypeptide and peptide designates a linear series of amino acid residues connected one to the other by peptide bonds between the alpha-amino and alpha-carboxy groups of adjacent residues. The term polypeptide is used somewhat interchangeably with peptide but, unless otherwise limited, is generally also used to include the proteins described herein.

The term "analog" includes any polypeptide having an amino acid residue sequence substantially identical to a sequence specifically shown herein in which one or more residues have been conservatively substituted with a functionally similar residue and which displays the ability to mimic CRF-BP as described herein. Examples of conservative substitutions include: the substitution of one non-polar (hydrophobic) residue, such as isoleucine, valine, alanine, glycine, leucine or methionine for another; the substitution of one polar (hydrophilic) residue for another, such as arginine for lysine, glutamine for asparagine, threonine for serine; the substitution of one basic residue such as lysine, arginine or histidine for another; and the substitution of one acidic residue, such as aspartic acid or glutamic acid for the other. The phrase "conservative substitution" also includes the use of a chemically derivatized residue in place of a non-derivatized residue provided that such polypeptide displays the requisite binding activity. "Chemical derivative" refers to a subject polypeptide having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to from O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions of residues relative to the sequence of a polypeptide whose sequence is shown herein, so long as the requisite biological activity is maintained.

As used herein, the terms "pharmaceutically acceptable", "physiologically tolerable" and grammatical variations thereof, as they refer to compositions, carriers, diluents and reagents, are used interchangeably and represent that the materials are capable of administration to a mammal without the production of undesirable physiological effects such as nausea, dizziness, gastric upset and the like.

The term "homolog" used herein refers to analogous proteins, peptides and DNA sequences from heterologous mammalian species that have evolved insignificant changes but perform the same biological function in substantially the same way.

The term "biologically active fragment" as used herein refers to fragments of the disclosed proteins or peptides which have been truncated with respect to either the N- or C-termini, or both; or the 5' or 3' end, or both, of the corresponding DNA coding regions, which fragments perform substantially the same or a directly related function or encode peptides which perform substantially the same or a directly related function as the precursor. "Modulating the transactivation of CRF receptors or modulating the action of CRF in mammals" as used herein comprises administering a therapeutically effective amount of a physiologically tolerable composition containing a brain-derived CRF-BP protein or biologically active fragment or homolog thereof to complex with CRF and/or dissociate the afore-described CRF-BP/CRF-BP complexes and likely complexes between 35 kD proteins and thereby modulate CRF actions in mammals by means of direct or induced antagonistic (competitive) association with endogenous CRF thus lowering the ambient in vivo concentration of CRF.

CRF binding proteins obtained from detergent solutions of sheep and rat brain cells were isolated with full retention of CRF binding activity. To obtain these binding protein molecules, mammalian brains were appropriately homogenized, treated, extracted and the isolated CRF-BPs were characterized. It is convenient to process groups of 3 sheep brains per isolation, as described in detail hereinafter in Example I.

Ovine CRF-BPs of 33 kD and 35 kD were purified from sheep brain as described in Example I and individually tested. CRF-binding protein-like immunoreactivity was detected in these 2 bands using a CRF-BP ligand immunoradiometric assay (LIRMA) as set forth in Example I. To demonstrate their affinities for CRF, the isolated brain ovine CRF-BP proteins are each cross-linked to either OCRF or hCRF using disuccinimidyl suberate as a bifunctional cross-linking agent. Each is found to bind to $^{125}$I-radiolabeled hCRF and OCRF. To further characterize these isolated proteins, binding assay experiments, as well known in the art, are also carried out with the purified membrane-associated CRF-BP proteins to determine the affinity at which they bind to CRF. The results of these assays are expressed in terms of the dissociation constant $K_D$, which is equal to the reciprocal of the concentration of free CRF at the equilibrium point where one-half of the CRF-BP present is bound to, i.e. complexed with, CRF. In other words, when the binding protein has a high affinity and binds CRF strongly, a low CRF concentration will half-saturate the total amount of binding protein molecules. Generally, a dissociation constant of about 5 or lower is considered to be an indication of strong affinity, and a $K_D$ of about 6 to 14 is an indication of intermediate affinity. The 33 kD molecule binds hCRF with strong affinity having a $K_D$=0.25±0.2 nanomolar. The 35 kD membrane-associated binding protein, which is an N-terminally extended version of the 33 kD protein, has a $K_D$=7.5±2.5 nM. Accordingly, slightly shorter membrane-associated binding proteins than the 33 kD protein are considered to also have similar strong binding affinities. Furthermore, the isolated ovine CRF-BPs are found to be specifically competed with cold CRF at a concentration of about 1 μM, showing that these proteins are indeed selectively complexing with the 41-residue CRF molecule.

These membrane-associated CRF-BPs, including those which bind to CRF with an intermediate affinity, e.g. between about 6 and about 15 nanomolar, are particularly useful in promoting the delivery of CRF to the cell surface receptors where its biological activity comes to fruition. Because both of these isolated ovine brain binding proteins bind to CRF, it is clear that binding proteins having N-termini intermediate therebetween would exhibit generally similar binding affinity. Moreover, it is considered that binding proteins further shortened from the N-terminus of the 33 kD protein by the elimination of one or a sequence of residues would also exhibit intermediate binding affinity.

As described hereinafter in detail, the 35 kD protein was found to have the 295 AA sequence set forth in SEQ ID NO:1 following a series of different experimental procedures.

N-terminal Edman degradation was individually performed on the two isolated brain ovine CRF-BPs by applying each of the isolated proteins to gas phase sequence analysis after SDS-PAGE and electrotransfer to a PUDF membrane. N-terminal sequence analysis of the 35 kD band revealed a protein containing the N-terminal amino acid (AA) sequence: Glu-Ala-Val-Asp-His-Asp-Ser-Phe-Pro-His-Leu-Ala-Gly-Ala-Ser (residues 1–16 of SEQ ID NO:1). N-terminal sequence analysis revealed the 33 kD band to contain a protein containing the N-terminal amino acid (AA) sequence: Glu-Leu-Glu-Gly-Glu-Pro-Leu-Tyr-Arg-Arg-Ala-Leu-Arg-Cys-Val-Asp-Met-Leu (residues 20–37 of SEQ ID NO:1).

Tryptic digestion of these purified proteins, followed by purification of the tryptic fragments, was also carried out. There were fragments among the tryptic fragments of the 35 kD protein which corresponded to all of the purified tryptic fragments of the 33 kD protein.

N-terminal sequence analysis was then carried out of these tryptic fragments and resulted in identification of the following N-terminal AA sequences:

Phe-Pro-Ser-Ser-Gln-Asp-His-Pro-Leu-Pro-Thr (residues 96–106, of SEQ ID NO:1);

Tyr-Val-Asp-Phe-Cys-Asp-Ser-Gly-Leu-Ser-Arg (residues 110-120 of SEQ ID NO:1);
Ser-Ser-Ala-Gly-Cys-Gly-Gly-Ile-Gly-Asp-Phe-Val-Glu-Leu-Leu-Gly-Gly (residues 206–222 of SEQ ID NO:1);
Val-Gly-Cys-Asp-His-Thr-Val-Leu-Arg (residues 248–256 of SEQ ID NO:1); and
Val-Thr-Phe-Glu-Tyr-Arg (residues 267–272 of SEQ ID NO:1). The presence of the Cys residues was deduced from the totality of experimental information obtained.

Following the purification and characterization of the 33 and 35 kD brain-derived ovine CRF-BPs by identification of multiple AA sequences, synthetic 5' sense and 3' antisense oligonucleotides directed to separate presumed DNA coding regions were used to clone ovine CRF-BP gene fragments by means of Polymerase Chain Reaction (PCR) from sheep CDNA (derived from sheep brain mRNA). Two ovine CRF-BP cDNA coding region clones of 552 and 441 base pairs (bp) are obtained as set forth herein as SEQ ID NO:3 and SEQ ID NO:4, respectively. In addition, a labelled CRF-BP cDNA coding region was then used as a molecular hybridization probe to obtain a gene segment from a lambda Zaph (Stratagene, La Jolla, CA) cDNA library made from ovine brain mRNA. The probe was successful in identifying a 678 bp ovine CRF-BP partial gene cDNA segment (SEQ ID NO:5) in the sheep brain cDNA library.

Subsequent comparison of the corresponding amino acid sequences from the Edman degradation N-terminal sequence analyses, the PCR-cloned cDNA coding regions, and the partial CDNA coding region yields a composite amino acid sequence of the 35 kD ovine CRF-BP (SEQ ID NO:1) and of the 33 kD ovine CRF-BP (residues 20–295 of SEQ ID NO:1). By comparison of the 2 PCR-cloned segments, it is deduced that there is a protein (SEQ ID NO:2) having a deletion of 37 AA residues corresponding to the 35 kD ovine CRF-BP and also a protein (residues 20–258 of SEQ ID NO:2) corresponding to the 33 kD ovine CRF-BP. Also deduced is the biologically active N-terminal, 18 or 19 AA residue, proteolytic cleavage product of the 35 kD ovine CRF-BP (residues 1–18 or 1–19 of SEQ ID NO:1). There are human membrane-associated CRF-BP proteins of about 33 kD and about 35 kD in the human brain, which are homologous to the ovine CRF-BPs, as there also are in rat brain.

The 35 kD ovine protein from brain has some sequences in common with the C-terminal portion soluble human serum CRF-BP (SEQ ID NO:6), which has now been expressed recombinantly. It has been determined that the mature human serum CRF-BP contains 5 disulfide bridges located linearly throughout the molecule, respectively between $Cys^{36}$ and $Cys^{57}$, $Cys^{80}$ and $Cys^{117}$; $Cys^{159}$ and $Cys^{181}$, $Cys^{213}$ and $Cys^{240}$, and $Cys^{253}$ and $Cys^{294}$ in SEQ ID NO:6. It is considered that a similar linkage pattern exists in the ovine purified proteins. In ovine brain-derived CRF-BP having the 37 AA deletion, at least one cysteine-cysteine potential loop is missing, which would cause the tertiary structure of such brain CRF-BP to be substantially different from that of the isolated 35 kD ovine brain protein and the secreted serum form of the human CRF-BP. Moreover, the very substantial structural differences in the region of the N-terminus of the brain-derived CRF-BPs from the structure of the soluble serum CRF-BP proteins are believed to contribute to their association with neuro-membranes and their function in the brain.

The ovine CRF-BP mRNA internal deletion represented by the cDNA PCR clone (SEQ ID NO:4) and the composite amino acid sequence (SEQ ID NO:2) is believed to be a result of alternate mRNA splicing. This results in the loss of the first disulfide loop in secondary structure and demonstrates the diversity of CRF-BPs as herein disclosed.

The 33 kD brain-derived ovine CRF-BP which lacks the 19-amino acid N-terminal domain represents 70% of the ovine brain-derived membrane-associated CRF-BP in vivo and binds CRF with high affinity as described supra. This 33 kD membrane-associated CRF-BP also has been demonstrated to physically complex with the 35 kD membrane-associated CRF-BP, and it is believed that this complexing is via the 19-residue N-terminus of the larger biomolecule as a result of assays performed using an antibody that is specific thereto. During the biological existence of such a 33 kD/35 kD CRF-BP complex or a similar 35 kD/35 kD complex in vivo, the high affinity CRF binding sites of both complexed CRF-BPs are unavailable or of substantially lesser binding affinity. This results in an vivo relative increase in ambient CRF which is free to bind synaptic sites. Furthermore, the 19-residue N-terminal proteolytic cleavage product of the 35 kD CRF-BP is biologically active to dissociate the 33 kD/35 kD CRF-BP complex, thus freeing the high affinity CRF binding sites, the result of which reduces the level of CRF available to bind synaptic receptors. Therefore, this peptide is considered therapeutically valuable in its ability to decrease the level of CRF available in the brain. Homolog versions of this peptide are present in other mammalian species, including humans where the N-terminal sequence of SEQ ID NO:6, e.g. residues 1–21, is considered to exert a similar biological function. The 18 and 19 residue N-termini of the 35 kD ovine brain-derived membrane-associated CRF-BP (residues 1–18 and 1–19 of SEQ ID NO:1) are also medically valuable for the design of chemical derivatives, analogs and comprehensive pharmaceutical compound designs. It is considered that this described family of compounds may be used to direct the activity of CRF to the vicinity of specific organs. The peptides/compounds are medically perceived to provide valuable therapeutics, for instance, in the treatment of local inflammation.

A full length CDNA ovine CRF-BP gene segment (SEQ ID NO:7) was subsequently cloned from the sheep brain cDNA library, from which it is deduced that the 35 kD protein is transcribed with a 29-residue leader sequence.

Naturally occurring CRF-BP proteins constitute only minor constituents of normal mammalian membranes, being present in only very impure form, relative to other native proteins also present. Because of the work involved, the limited availability of biological samples, and the relatively low concentration in mammalian brain, it would be impractical to prepare CRF-BP by purification from natural sources. Therefore, brain-derived membrane-associated CRF-BPs are not practically available for clinical use or in the comprehensive design of analogous pharmaceutical compounds unless recombinant DNA production of the proteins and/or analogs are enabled, which of course entails knowing the entire amino acid structure of the native proteins as disclosed herein.

CRF-BP polypeptide fragments can be synthesized by any of the techniques that are known to those skilled in the polypeptide art, including recombinant DNA techniques. Synthetic chemistry techniques, such as solid-phase Merrifield-type synthesis, are also preferred for producing polypeptide fragments for reasons of purity, antigenic specificity, freedom from undesired side products, ease of production and the like.

Recombinant DNA techniques, for example, can be used to generate organisms or cell lines that produce the heterologous protein in significantly higher proportions, relative to total protein, in the cellular material and/or the secretions thereof; as compared to the proportions at which native CRF-BPs are present. Construction of synthetic genes which encode the ovine CRF-BPs, as well as other mammalian CRF-BPs, and therefore recombinant expression of these proteins is made feasible by the amino acid sequences disclosed herein. Because the starting material from which such synthetic recombinant CRF-BP proteins are isolated is from media which is essentially free of protein contaminants and has a substantially greater concentration of the heterologous protein, available purification techniques can fairly simply produce more highly purified CRF-BP preparations in relatively copious amounts. For example, expression of a synthetic DNA coding region corresponding to the amino acid sequence SEQ ID NO:1 in CHO cells can be effected using standard techniques to produce the 295-residue glycosylated protein. An exemplary recombinant production is described in Example IV. As a result, methods of treatment can be carried out by the administration of the recombinant proteins and their effective analogs. Examples of proteins and peptides which are advantageously employed include the 35 kD ovine CRF-BP (SEQ ID NO:1); the 33 kD ovine CRF-BP (residues 20–295 of SEQ ID NO:1); these two proteins with the 37 amino acid deletion (SEQ ID NO:2 and residues 20–258 of SEQ ID NO:2); N-terminal fragments of the mature 35 kD protein (SEQ ID NO:1), for example residues 1–18 or 1–19 (beginning with Glu and ending with Lys or Arg); and N-terminal fragments of the mature human serum protein (for example residues 1–21 of SEQ ID NO:6).

Pharmaceutical compositions will usually contain the peptides in conjunction with a conventional, pharmaceutically-acceptable carrier. For treatment, substantially pure isolated or synthetic CRF-BP or a nontoxic salt thereof, combined with a pharmaceutically acceptable carrier to form a pharmaceutical composition, is preferably administered parenterally to mammals, including humans, either intravenously (iv), subcutaneously, intramuscularly, percutaneously, e.g. intranasally, or introcerebroventricularly; oral administration is possible with an appropriate carrier.

Any polypeptide of the present invention may be used in the form of a pharmaceutically acceptable salt. Suitable acids which are capable of forming salts with the peptides of the present invention include inorganic and organic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di-, and tri-alkyl and -aryl amines (e.g., triethylamine, diisopropyl amine, methyl amine, dimethyl amine and the like) and optionally substituted ethanolamines (e.g., ethanolamine, diethanolamine, and the like).

Therapeutic compositions of the present invention may desirably contain a physiologically tolerable carrier together with a brain-derived CRF-BP protein, human homolog, polypeptide fragment or biologically active analog as described herein, dissolved or dispersed therein as an active ingredient. In a preferred embodiment, the therapeutic composition is not immunogenic when administered to a mammal or a human patient for therapeutic purposes.

The preparation of a pharmacological composition that contains active ingredients dissolved or dispersed therein is well understood in the art. Typically such compositions are prepared as injectables either as liquid solutions or suspensions; however, solid forms suitable for solution, or suspension, in liquid prior to use can also be prepared. The preparation can also be emulsified.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein which salts were hereinbefore described.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

Liquid compositions can also contain liquid phases in addition to and to the exclusion of water. Exemplary of such additional liquid phases are glycerin, vegetable oils such as cottonseed oil, and water-oil emulsions.

Administration of these CRF-BPs or certain polypeptide fragments thereof is effective to reduce high ACTH levels in mammals caused by excessive CRF, which is referred to herein as "CRF-induced ACTH release." In this manner, the CRF-BPs are useful in treating high cortisol (i.e., glucocorticoids) levels which are associated with hypercortisolemia, Cushing's Disease, alcoholism, anorexia nervosa and similar diseases. The CRF-BP proteins and fragments thereof are also useful to treat abnormalities which occur during the later stages of pregnancies; for example, they can be used to reduce pregnancy-induced complications and increased CRF levels which can otherwise result in excessive release of ACTH. In addition, CRF-BP proteins or fragments thereof can be administered to reduce the ratio of CRF/CRF-BP present in a patient. The iv administration of CRF-BPs may also be employed in certain instances to modulate blood pressure and thereby combat hypotension. The CRF-BP proteins can be effectively used to modulate the action of CRF on the brain, particularly with respect to control of appetite, reproduction, growth, anxiety, depression, fever and metabolism, as well as the regulation of blood pressure, heart rate and blood flow. As previously indicated, the short N-terminal fragments are also expected to be valuable in the brain.

Thus, the present invention provides for a method for modulating the action of CRF in mammals comprising administering a therapeutically effective amount of a physiologically tolerable composition containing a CRF-BP protein or polypeptide fragment of the present invention. A therapeutically effective amount is an amount calculated to achieve the desired effect, i.e., to decrease the amount of ACTH or decrease the CRF/CRF-BP ratio in a patient. The required dosage will vary with the particular treatment and with the duration of desired treatment. Very generally, daily dosages of between about 10 micrograms and about 1 milligram per Kg of body weight are presently contemplated, dependent however on the size of the protein or polypeptide, i.e. a relatively lesser amount might be employed of the short N-terminal fragments. In addition, changes in ACTH levels can be monitored during a treatment regimen to determine the effectiveness of the administered CRF-BP protein or polypeptide fragment over time. The level of ACTH present in a patient, can be readily determined by routine clinical analysis, and assays to monitor the level of ACTH are well known. Thus, the present therapeutic method also provides a way to decrease ACTH levels in a human patient.

Preparations of purified, isolated membrane-associated CRF-BP or recombinant protein are advantageously employed to inhibit CRF-induced ACTH release in vivo. Thus, these CRF-BPs can be administered therapeutically to bind to and inactivate CRF thereby reducing high ACTH levels in mammals caused by excess CRF. Moreover, they can be used to reduce pituitary ACTH secretion and hence reduce cortisol levels under any condition in which they are abnormally high, such as during chronic stress or in patients afflicted with anorexia nervosa or alcoholism. It has been found that CRF-BPs when administered intravenously (iv) have also proved effective to prevent CRF-induced ACTH release. Furthermore, it is considered that iv administration of the CRF-BPs can be used to raise blood pressure and in this manner combat hypotension.

These binding proteins can also be used in assay systems to monitor the effects of chemical modifications to CRF on its binding affinity, and they are useful for screening compounds in competitive binding assays and in assays useful to determine affinities for CRF receptors. Representative assays are disclosed in U.S. patent application Ser. No. 08/097,828, filed Jul. 23, 1993, which is commonly assigned, the disclosure of which is incorporated herein by reference. Their high binding affinity for human CRF makes these binding proteins particularly valuable for use in assays to determine CRF levels in body fluids, e.g. serum, and in tissue.

Methods of screening compounds for the therapeutically valuable property of the ability to cause in vivo dissociation of CRF-BP/CRF-BP complexes, e.g., the property to cause dissociation of the brain-derived 33 kD/35 kD or possibly of the 33 kD/N-terminal cleavage peptide complexes are herein enabled. For example, equimolar amounts of the ovine brain-derived 33 kD CRF-BP and 35 kD CRF-BP and an excess of radiolabelled CRF are mixed in an approximate physiological ionic and buffered solution. Then, after biological equilibrium is achieved, the putative therapeutic compound, i.e., a small peptide, or nonpeptide e.g., a steroid, is introduced into the solution to test whether dissociation occurs, thereby freeing the 35 kD CRF-BP and allowing it to bind CRF. Subsequent to kinetic equilibrium of the biological solution, purified antibody directed toward the N-terminus of the 35 kD CRF-BP is added. Upon re-equilibration under physiological conditions, the first antibody is precipitated with a second conjugate antibody or Staphlococcus protein A. In the case of the N-terminal peptides described supra or an effective drug candidate, the 35 kD CRF-BP/labelled CRF complex is thereby precipitated. Quantitative analysis is performed and compared by scintillation counting to determine the relative effectiveness of the putative therapeutic compound.

These CRF-binding proteins when coupled to a solid matrix can be used to isolate CRF from biological samples or from aqueous solution as a part of an affinity column or the like. The binding ability of these CRF-BPs allows them to be used in affinity chromatography to purify hCRF or homologs of CRF. These CRF binding proteins can be coupled to Sepharose or other suitable affinity chromatography supports and used to purify CRF and CRF analogs from solutions and biological samples.

The following examples describe certain of the experimental procedures which were employed and to which reference was variously made hereinbefore.

EXAMPLE I

To obtain the purified proteins which bind to CRF, three sheep brains were homogenized in 700 ml of standard binding buffer containing 50 mM sodium phosphate, 100 mM sodium chloride, 25 mM EDTA, 0.1 volume percent sodium azide (SPEA) containing 10 mM magnesium chloride, 2 mM phenylmethyl-sulfonylfluoride (PMSF), 2.8 $\mu$g/ml leupeptin and 7 $\mu$g/ml aprotinin. The homogenate was divided into 500 ml centrifuge buckets and spun at 3000 rpm for 10 minutes in a centrifuge to separate nuclei and particulate matter. The supernatant was decanted, and the pellet was solubilized by the addition of an aqueous solution of NP-40 liquid detergent at a concentration of about 0.2% by volume and by stirring at 4° C. for 1 hour. NP-40 (Nonidet P-40) is a detergent consisting of an octylphenol-ethylene oxide condensate containing an average of nine moles of ethylene oxide per mole of phenol; it is available from a number of suppliers, including Fluka Chemical Corporation and Sigma Chemical Company. The NP-40 employed was a >99% pure substance obtained from Fluka Chemika-BioChemika, Ronkonkoma, N.Y., 11779. The mixture was then re-centrifuged at 5000×g for 15 minutes at 4° C., and the supernatant was decanted. The resultant pellet was re-extracted by the addition of 400 ml of binding buffer, and the mixture was recentrifuged as described above without the addition of NP-40. The re-extraction procedure was repeated four times. All the resulting supernatants were pooled and then diluted to a final volume of 4 L with binding buffer.

1 ml of granular Affigel chromatographic media (BioRad) was washed with 50 ml of distilled water at 4° C. 1 mg of CRF was then dissolved in 7 ml of coupling buffer which was 100 mM Hepes, pH 7.4. The Affigel media was added to the mixture, and the container was rotated overnight at 4° C., allowing the CRF peptide to couple to the media in a total volume of 10 ml. The solid phase was then left to settle under gravity, and the supernatant was decanted. Unreacted groups on the Affigel media were then blocked by exposing the solid phase to 1M ethanolamine/HCL pH 8.0 and rotating in a suitable container for 1 hour at 25° C. The resulting CRF-solid phase conjugate was transferred to a sintered glass funnel and washed sequentially with ten 50 ml batches each containing 50 mM sodium acetate/formate/20% acetonitrile buffer, pH 3.0 and 100 mM Hepes pH 7.4. The CRF-solid phase conjugate was then finally diluted by thoroughly mixing with 9 mls of cold, unactivated granular Sepharose 4B, and this dilute mixture was used as the media for the 1st step of the affinity chromatographic separation.

Media for a 2nd step separation was prepared as described above except that no dilution with cold unactivated Sepharose 4B was used, so that the 1 ml of granular Affigel-CRF conjugate alone was employed to treat the much smaller volume of material.

The 4 liters of extract was then exposed to the 10 ml of diluted CRF-solid phase conjugate by stirring this chromatographic media with the extract overnight at 4° C. After exposure, the solid phase was recovered by filtering the 4 L extract through a coarse 600 ml sintered glass funnel. The solid phase was then washed off the sintered glass with 0.9% NaCl and transferred to a BioRad Econo column (20×2.5 cm) where it was further washed with approximately 200 mls of 0.9% NaCl. The bound proteins were then desorbed with 50 mL of elution buffer, i.e. 80% 50 mM sodium acetate-formate buffer/20% acetonitrile, pH 3.0, containing 0.1% by volume bovine serum albumin (BSA); ten 5 ml fractions were sequentially collected throughout this elution.

Each of the fractions was assayed for CRF-BP-like immunoreactivity with the aid of a CRF-BP ligand immunoradiometric assay (LIRMA) which utilized an antibody (Ab 5144) raised against the entire human recombinant mature protein hCRF-BP(1-298). The assay utilized CRF-BP antibody 5144 at 1:1000 initial dilution, and a high affinity radiolabeled $^{125}$I-hCRF trace [50,000 c.p.m.]. 50 μl of radio-iodinated CRF trace [diluted to 50,000 c.p.m./50 μl in assay buffer] is added to a silicate glass tube containing an aliquot from each fraction followed by incubation for 30 minutes at room temperature to allow binding to occur. CRF-BP antibody 5144, i.e. 50 μl, diluted 1:1000 in assay buffer (SPEA containing 0.25% B.S.A. and 10 mM MgCl$_2$), is then added to each glass tube and incubated for a further 30 minutes at room temperature. If desired to obtain competitive binding curves as a part of an assay of this type, binding is allowed to occur in the presence of a series of cold CRF concentrations ranging from 0 to 1000 nM. Bound complexes are then precipitated by the addition of 200 μl of precipitated sheep anti-rabbit [SAR] second antibody [a mixture containing SAR1:20, 1% NRS, 4% PEG, 50 mM sodium phosphate, 0.1% sodium azide], followed by incubation for 30 minutes at room temperature. The antibody-bound-$^{125}$I-CRF precipitate is then separated by centrifugation [3000×g ] at 4° C. for 20 minutes, and the resulting pellets are counted in a gamma counter.

Active fractions were then pooled, and the pH was adjusted to about 7.5 with 1M tris base, providing approximately 15 ml of eluant. This eluant was then percolated at 4° C. 5 times over the undiluted CRF-solid phase conjugate which had been loaded into a BioRad Econo column (0.7×10 cm). The solid phase conjugate column was then washed sequentially with 40 mls of 0.9% NaCl and 15 mls of 80% 50 mM sodium acetate-formate/20% acetonitrile buffer, pH 6.8. Bound proteins were then finally eluted in five 0.5 ml fractions using the same elution buffer which was used in eluting the proteins from the first affinity chromatography step but without including any BSA.

The active fractions which eluted from this solid phase column and which bound to Ab 5144, as determined by LIRMA, were pooled and then concentrated to approximately 100 μl under vacuum in a Speed-Vac™ concentrator. These concentrates were then reduced by the addition of SDS sample buffer containing 5% mercaptoethanol in an amount of about 4 times their volume, and the pH was adjusted to approximately neutral by the addition of 5M NaOH, dropwise, until the sample buffer color changed from yellow to pale blue. The concentrates were then subjected to SDS electrophoresis on 10% SDS polyacrylamide gels for 4 hours at 25° C. The separated proteins were then transferred onto Immobilon-P blotting membrane by performing horizontal electrophoresis for 45 minutes at 25° C. in a BioRad transblot apparatus, utilizing 100 mM 3-[cyclohexylamino]-1-propanesulfonic acid (CAPS), pH 11, buffer containing 10% methanol as the transfer buffer. Protein bands were then visualized by staining the Immobilon membrane with Amido black staining solution for 5 minutes at room temperature.

Prominent bands were observed corresponding to 33 and 35 kD. Stained protein bands were then cut out from the Immobilon membrane, which is a polyvinylidene fluoride (PVDF) membrane, and they were stored until use in Eppendorf tubes containing 1 ml of distilled water which are frozen at −70° C. The procedure as described in this example is repeated using 2 more groups of three sheep brains each, and a similar staining pattern is obtained each time on the Immobilon membrane.

The procedure as described is repeated using groups of 500 rat brains each, and a similar staining pattern is obtained each time on the Immobilon membrane. Similar results are obtained using human brain tissue.

EXAMPLE II

The two isolated 35 kD and 33 kD brain-derived membrane-associated ovine CRF-BPs from Example I were characterized by determining amino acid sequence data in the following manner.

N-terminal Edman degradation was individually performed on the isolated brain ovine CRF-BPs by applying each of the isolated proteins to gas phase sequence analysis after SDS-PAGE and electrotransfer to a PUDF membrane. N-terminal sequence analysis of the 35 kD ovine CRF-BP revealed a protein containing the N-terminal amino acid (AA) sequence: Glu-Ala-Val-Asp-His-Asp-Ser-Phe-Pro-His-Leu-Ala-Gly-Gly-Ala-Ser (residues 1–16 SEQ ID NO:1). N-terminal sequence analysis revealed the isolated 33 kD ovine CRF-BP to contain a protein containing the N-terminal amino acid (AA) sequence: Glu-Leu-Glu-Gly-Glu-Pro-Leu-Tyr-Arg-Arg-Ala-Leu-Arg-Cys-Val-Asp-Met-Leu (residues 20-37 SEQ ID NO:1).

Tryptic digestion of the purified ovine CRF-BP proteins is carried out, followed by purification of the tryptic fragments. The tryptic fragments from the 33 kD fraction all have counterparts in the tryptic digest pattern of the 35 kD protein. Sequence analysis of five separate tryptic fragments, following N-terminal sequencing of those fragments, produced the following AA sequences:

Phe-Pro-Ser-Ser-Gln-Asp-His-Pro-Leu-Pro-Thr (residues 96–106 SEQ ID NO:1);

Tyr-Val-Asp-Phe-Cys-Asp-Ser-Gly-Leu-Ser-Arg (residues 110–120 SEQ ID NO:1);

Ser-Ser-Ala-Gly-Cys-Gly-Gly-Ile-Gly-Asp-Phe-Val-Glu-Leu-Leu-Gly-Gly (residues 206–222 SEQ ID NO:1);

Val-Gly-Cys-Asp-His-Thr-Val-Leu-Arg (residues 248–256 SEQ ID NO:1); and

Val-Thr-Phe-Glu-Tyr-Arg (residues 267–272 SEQ ID NO:1). The Cys residues were deduced from overall experimental data.

Following obtaining the N-terminal sequence data from the purified 33 and 35 kD brain-derived ovine CRF-BPs and these tryptic fragment sequence analyses, synthetic 5' sense and 3' antisense oligonucleotides of 21 bases each with about 55% G,C content were obtained which were directed to coding regions that were felt to be highly conserved between different mammalian species. These oligonucleotides were used to clone ovine CRF-BP gene fragments by means of Polymerase Chain Reaction (PCR) from ovine cDNA (derived from brain mRNA). Using standard PCR conditions and 35 cycles of 94° C. denaturation, 45° C. annealing, 72° C. extension, with one final extension for 10 min. at 72° C., DNA fragments of 552 and 441 base pairs (bp) were produced. These ovine CRF-BP cDNA partial clones are set forth herein as SEQ ID NO:3 and SEQ ID NO:4, respectively.

A 621 base pair pst1 fragment from the 5' end of the human serum CRF-BP cDNA coding region was labeled and used as a molecular hybridization probe to screen the lambda Zap™ sheep brain CDNA library described supra. A 678 bp ovine CRF-BP cDNA partial clone (SEQ ID NO:5) was identified.

Subsequent comparison of the corresponding amino acid sequences from the Edman degradation sequence analyses, the PCR cloned cDNA fragments, and the cDNA partial clone yields the composite amino acid sequence of the 35 kD ovine CRF-BP (SEQ ID NO:1); of the 33 kD ovine CRF-BP (residues 20–295 of SEQ ID NO:1); and of these two proteins with the 37 amino acid deletion (SEQ ID NO:2 and residues 20–258 of SEQ ID NO:2). The biologically active N-terminus which is proteolytically cleaved from the 35 kD ovine CRF-BP is also identified as residues 1–18 or 1–19 of SEQ ID NO:1.

EXAMPLE III

Ovine brain-derived membrane-associated CRF-BP Binding and Dissociation Analyses:

Antibodies directed to the peptide comprising N-terminal residues 1–25 of SEQ ID NO:6 (human CRF-BP) are able to immunoprecipitate the CRF/human CRF-BP complex. The same antibodies do not have immunoaffinity to the full length ovine 33 or 35 kD ovine brain-derived membrane-associated CRF-BPs. These antibodies with affinity toward the human CRF-BP N-terminus are not able to bind the full length human CRF-BP of SEQ ID NO:6 when 33 kD ovine brain-derived CRF-BP is added to the solution. It is thus concluded that the N-terminal epitope region of the human CRF-BP is masked from the antibody in the human CRF-BP/33 kD ovine brain-derived CRF-BP complex. It is furthermore shown that a synthetic peptide consisting of human residues 1–21 of SEQ ID NO:6 inhibits the ability of ovine CRF-BP to bind CRF, but it does not inhibit the ability of full length human serum CRF-BP to bind CRF. This is due to 70% of the brain-derive ovine CRF-BP being composed of the N-terminal truncated version (33 kD) of the 35 kD ovine CRF-BP. Therefore it is most probable that residues 1–21 of SEQ ID NO:6 (human CRF-BP) complex with the 33 kD brain-derive ovine CRF-BP but not with the full length 35 kD ovine protein. The ovine 35 kD brain-derived CRF-BP is therefore analogous to the human serum-derived CRF-BP; whereas the 33 kD truncated version and the N-terminal proteolytic cleavage product are brain-derived mammalian entities with different functions.

The synthetic 21 amino acid N-terminal human serum CRF-BP peptide does not, in itself, have affinity for CRF. The N-terminal ovine CRF-BP peptides, i.e. residues 1–18 and 1–19 of SEQ ID NO:1, likewise do not complex with CRF. The 33 kD ovine protein, however, binds CRF with high affinity (D of 0.25). Moreover, the 21-residue synthetic N-terminal human serum CRF-BP inhibits formation of the CRF/33 kD ovine CRF-BP complex.

The 35 kD ovine CRF-BP serves partially as a precursor from which the 33 kD protein and 18 and 19 residue N-terminal proteolytic fragments are derived. The proteolytic cleavage may occur between residues 19–20 of SEQ ID NO:1 or between residues 18 and 19, with the Arg residue subsequently being trimmed. In any event, it results in a conformational change in the ovine brain-derived CRF-BP that decreases its 4 for CRF from 7.5 to 0.25 nanomolar. The resulting 33 kD CRF-BP also has a tendency to complex with the 35 kD ovine CRF-BP, which complex occurs through the N-terminus of the 35 kD protein to create 35 kD/33 kD ovine CRF-BP complex. Thus, the 35 kD ovine CRF-BP with its intact and exposed N-terminal 19 residue region is reactive to complex with the 33 kD version; however, the N-terminal cleaved 18 and 19 AA peptides are able to compete with the 35 kD protein and cause dissociation of the complex of the 35 kD ovine CRF-BP and the 33 kD ovine CRF-BP. It is expected that this N-terminal proteolytic product and its human brain homolog will hence be able to liberate CRF-BP CRF binding sites and thereby increase binding site density for CRF in biological tissues. This will effectively reduce the concentration of CRF in biological tissues and is therefore reasonably expected to be useful for the treatment of high level CRF related physiological disorders.

The proteolytic event which produces the 33 kD version of the brain-derived CRF-BP is important in governing the brain ratio of the 33 kD CRF-BP to the 35 kD CRF-BP. This proteolytic event therefore is critical in determining the equilibrium level of unbound CRF in the brain. The natural control mechanism in which such a brain protease partakes is a fine tuning device to control the 33/35 kD CRF-BP molecular population in the brain and thus the amount of available synaptic CRF binding sites. Therefore, therapeutically valuable peptide and analog antagonists of this protease can be provided in the form of CRF-BP fragments and synthetic chemical derivatives or analogs of sufficient length to be recognized by the native proteolytic enzyme and which also span the native cleavage site (i.e. residues 18–19 of SEQ ID NO:1 and residues 21–22 of SEQ ID NO:6). Such peptides are at least about 5 residues in length, are preferably greater than about 10 AA residues in length, and more preferably are about 15 residues or more.

EXAMPLE IV

The construction of functional genes which encode the ovine CRF-BPs is set forth hereinafter as well as methods for recombinant expression of these proteins. DNA coding regions for the mature 35 kD ovine brain-derived membrane-associated CRF-BP are constructed by fusion, in 5′-3′ order of: (1) a synthetic DNA sequence which encodes residues 1–7 (using the statistically conserved human codons of the genetic code for these particular residues well known to those skilled in the art) of SEQ ID NO:1, (2) the 1–189 bp DNA sequence of SEQ ID NO:3, and (3) the DNA sequence of SEQ ID NO:5. Heterologous gene expression of this composite DNA segment contains the complete coding region for the mature 35 kD protein (SEQ ID NO:1) and is effectively carried out in Chinese hamster ovary (CHO) cells, CV-1 cells, HeLa S3, NIH-3T3 cells or COS7 cells using either commercially available expression vectors such as pMSG, pSVT7 and pMT2 from Pharmacia, Piscathaway, N.J., or the widely used Okayama-Berg vectors. Use of standard techniques produces the 295-residue active mature glycosylated protein (see also, E. Potter, et al., *Nature,* 349, 423–426 (Jan. 31, 1991); *Molecular Cloning, A Laboratory Manual* 2Ed, Chapter 16, Expression of Cloned Genes in Cultured Mammalian Cells, J. Sambrook et al. (1989)). Baculovirus vectors may also be used for heterologous expression of these genes in cultured insect cells as described by Summers, M. D. et al., *Tex. Agric. Exp. Stn. Bull.* No. 1555 (1987). This composite DNA segment gene can alternatively be fused to native bacterial genes to create stable chimeric procaryotic biosynthetic proteins. The chimeric proteins are easily isolated by affinity chromatography, and the active protein is then released by subsequent site-specific proteolytic cleavage. Well developed commercial bacterial expression vectors and host cells are readily available, as well as isolation/purification materials and protocols for production of these biosynthetic polypeptides (i.e. Protein Fusion and Purification system (PFP), New England Biolabs).

The evidentiary lack of digression in evolution in regard to the molecular structure of the 41 AA CRF biological messenger between rats and humans is fairly indicative of probable conserved regions in the corresponding amino acid sequences of analogous receptors and CRF brain-derived binding proteins in such diverse mammalian species. The corollary is that, once one has a significant portion of a brain-derived membrane-associated CRF-BP nucleic acid sequence of one mammalian species, i.e. the ovine sequence as disclosed herein, it is a straightforward exercise to obtain naturally occurring variant homolog sequences of other animal species which encode homolog binding proteins (see e.g., Potter et al., *Nature,* 349, 423–426 (1991), where it was shown that the cDNA coding region for human serum-derived CRF-BP was of sufficient homology to permit identification of an analogous serum-derived rat cDNA coding region). For example, using established methods well known to those skilled in the art (see e.g., *Molecular Cloning, A Laboratory Manual* 2Ed, Chapter 8, Construction and Analysis of cDNA Libraries, J. Sambrook et al. (1989)), SEQ ID NOs:3–5 or portions thereof may be used to screen mammalian cDNA libraries made from human brain mRNA to identify and isolate human brain-derived membrane-associated CRF-BP DNA homolog coding regions and/or those of other mammalian species.

EXAMPLE V

CRF-BP can be used to determine whether CRF is present in a sample in accordance with the following protocol. An appropriate assay can be implemented in various ways. For instance, the CRF-BP could be coupled to a 96-well microtiter plate, and aliquots of the samples prospectively containing CRF can then be incubated with the bound CRF-BP in the presence of a fixed amount of authentic CRF with biotin coupled to it. After a 4–6-hour incubation, the solutions would be removed and the plates washed to remove unbound CRF. Adding avidin coupled to horseradish peroxide (HRP) and incubating forms a complex with the CRF-biotin conjugate. Again, the plates would be washed and HRP substrate added. Color would develop most in wells containing samples with no CRF. As the sample continued to be incubated, the biotin-CRF conjugate would bind at decreasing levels; hence, the color development would be less. This would give a dose-dependent response that could be calibrated using authentic CRF (as appropriate) of known concentration. This type of assay has the advantages of a radioreceptor assay, including the specificity for active ligand capable of binding to the receptor, and the sensitivity and simplicity of an ELISA antibody assay, without the disadvantages of either (i.e., radioactive tracer, non-specificity for active protein).

Unless otherwise stated hereinbefore, all percentages are volume percents.

Although the invention has been described with regard to its preferred embodiments, which constitute the best mode permanently known to the inventors, it should be understood that various changes and modifications as would be obvious to one having the ordinary skill in this art may be made without departing from the scope of the invention which is set forth in the claims appended hereto. For example, biologically active fragments of such proteins, shortened at the C-terminus or at the N-terminus or at both termini, can be employed instead of the entire protein to have the same biological effect of modulating the bioactivity CRF.

Particular features of the invention are emphasized in the claims which follow.

We claim:

1. An isolated and purified DNA segment that encodes a CRF-binding protein which exhibits affinity to CRF, which has a molecular weight of at least about 33 kD as determined under reducing conditions by SDS PAGE, and which has the amino acid sequence of a native mammalian protein that includes at least one sequence selected from the group consisting of the following sequences of SEQ NO: 1:

residues 1–16, residues 20–37, residues 110–120, residues 206–222 and residues 248–256.

2. A DNA segment according to claim 1 wherein said CRF-binding protein has sufficient amino acid sequence that it binds to hCRF such that its dissociation constant ($K_D$) is about 10 nanomolar or less.

3. A DNA segment according to claim 1 which encodes a CRF-binding protein having a molecular weight of about 35 kD and an N-terminus of residues 1–16 of SEQ ID NO: 1.

4. A DNA segment according to claim 1 which encodes a CRF-binding protein comprising residues 1–295 of SE D NO:1.

5. A DNA segment according to claim 1 which encodes a CRF-binding protein having a molecular weight of about 33 kD and an N-terminus of residues 20–37 of SEQ ID NO: 1.

6. A DNA segment according to claim 5 which encodes a CRF-binding protein comprising residues 20–295 of SEQ ID NO:1.

7. A DNA segment according to claim 1 comprising SEQ ID NO:3.

8. A DNA segment according to claim 1 comprising SEQ ID NO:5.

9. A DNA segment according to claim 1 which encodes CRF-binding protein having SEQ ID NO: 2.

10. A DNA segment according to claim 1 which encodes a CRF-binding protein comprising the amino acid residue 20–258 of SEQ ID NO: 2.

11. A DNA segment according to claim 1 comprising SEQ ID NO: 4.

12. A method of producing a CRF-binding protein, which method comprises culturing recombinant host cells transformed with an expression vector which includes a DNA segment of claim 1 which is capable of effecting expression of said DNA, said culturing being carried out under conditions which permit the expression of said DNA and recovery of the protein.

* * * * *